(12) United States Patent
McNames et al.

(10) Patent No.: US 8,057,398 B2
(45) Date of Patent: Nov. 15, 2011

(54) METHOD, SYSTEM, AND APPARATUS FOR CARDIOVASCULAR SIGNAL ANALYSIS, MODELING, AND MONITORING

(75) Inventors: James McNames, Portland, OR (US); Pedro Mateo Riobo Aboy, Scottsdale, OR (US)

(73) Assignees: APDM, Inc., Portland, OR (US); State of Oregon by and through the State Board of Higher Education on Behalf of Portland State University, Portland, OR (US)

( * ) Notice: Subject to any disclaimer, the term of this patent is extended or adjusted under 35 U.S.C. 154(b) by 46 days.

(21) Appl. No.: 12/200,995

(22) Filed: Aug. 29, 2008

(65) Prior Publication Data

US 2009/0069647 A1 Mar. 12, 2009

Related U.S. Application Data

(60) Provisional application No. 60/969,333, filed on Aug. 31, 2007.

(51) Int. Cl.
*A61B 5/02* (2006.01)
(52) U.S. Cl. ...................................... 600/481
(58) Field of Classification Search .................. 600/481, 600/485, 500, 504, 508
See application file for complete search history.

(56) References Cited

U.S. PATENT DOCUMENTS

| | | | | |
|---|---|---|---|---|
| 6,413,223 | B1 * | 7/2002 | Yang et al. | 600/485 |
| 7,215,986 | B2 * | 5/2007 | Diab et al. | 600/336 |
| 2002/0137994 | A1 * | 9/2002 | Baker et al. | 600/310 |

OTHER PUBLICATIONS

McNames et al., "Cardiovascular Signal Decomposition and Estimation with the Extended Kalman Smoother", Aug. 30-Sep. 3, 2006, Proceedings of the 28th IEEE: EMBS Annual International Conference, p. 3708-3711.*

Van Der Mewre, Rudolph; "Sigma-Point Kalman Filters for Probabilistic Inference in Dynamic State-Space Models"; Apr. 2004; dissertation submitted to OGI School of Science & Engineering at Oregon Health & Science University.*

McNames J; Aboy M; "Cardiovascular Signal Decomposition and Estimation with the Extended Kalman Smoother", EMBS Annual International Conference, Aug. 30-Sep. 3, 2006.

* cited by examiner

*Primary Examiner* — Patricia Mallari
*Assistant Examiner* — Christian Jang
(74) *Attorney, Agent, or Firm* — Aboy&Associates PC; Mateo Aboy

(57) ABSTRACT

Disclosed embodiments of the invention include a method, system, and apparatus to monitor cardiovascular signals such as arterial blood pressure (ABP), pulse oximetry (POX), and intracranial pressure (ICP).

The system can be used to calculate and monitor useful clinical information such as heart rate, respiratory rate, pulse pressure variation (PPV), harmonic phases, pulse morphology, and for artifact removal. The method uses a statistical state-space model of cardiovascular signals and a generalized Kalman filter (EKF) to simultaneously estimate and track the cardiovascular parameters of interest such as the cardiac fundamental frequency and higher harmonics, respiratory fundamental frequency and higher harmonics, cardiac component harmonic amplitudes and phases, respiratory component harmonic amplitudes and phases, and PPV.

20 Claims, 4 Drawing Sheets

(a) Heart Rate Estimation from the Patient Monitor based on ECG (b) Heart Rate Estimation from ABP

METHOD, SYSTEM, AND APPARATUS FOR CARDIOVASCULAR SIGNAL ANALYSIS, MODELING, AND MONITORING

CROSS REFERENCE TO RELATED APPLICATIONS

This application claims the benefit of P patent application No. 60/969,333 filed on Aug. 31, 2007 by the present inventors, which is incorporated by reference.

BACKGROUND

Technical Field

Disclosed embodiments relate to medical devices. Specifically, disclosed embodiments relate to medical devices and methods for analysis and monitoring of cardiovascular signals.

BACKGROUND

Cardiovascular signals contain parameters of clinical significance that must be estimated, but have a complicated nonlinear relationship to the observed signals. For instance, accurate estimation and tracking of the heart and respiratory frequencies from ABP, POX, and ICP is important for algorithms embedded in patient monitors in the emergency room and intensive care applications. Commercial monitoring systems often include the capability to monitor heart rate and several statistics of pressure signals such as the systolic, diastolic, and mean, but few can reliably estimate other components of pressure waveforms such as the respiratory rate, pulse pressure variation (PPV), harmonic phases, or pulse morphology.

Currently available systems are empirical in nature and do not used an underlying statistical model to estimates and automatically track all the cardiovascular parameters of interest and solve clinically important problems such as: 1) estimation and tracking of heart rate from pressure signals, 2) estimation and tracking of respiratory rate from pressure signals, 3) model-based filtering, artifact removal, and interpolation, 4) cardiovascular signal decomposition, characterization, and tracking of pulse morphology, and 5) PPV estimation on mechanically ventilated subjects during periods of abrupt hemodynamic monitoring These problems have important clinical significance. For instance, accurate estimation and tracking of PPV is important, since numerous studies have found that PPV is one of the most sensitive and specific predictors of fluid responsiveness and PPV is used to optimize fluid therapy [1-6]. Characterization and tracking of the ICP pulse morphology during intracranial hypertension is also important. Several research studies have indicated ICP morphology changes correlate with a deterioration of the mechanisms that control ICP [7,8, 8-11], and great interest exists in developing indices [8,10-14] to characterize and track the pulse morphology in order to understand how such changes in morphology are related to intracranial compliance, cerebral autoregulation (CAR), and outcome. Accurate tracking of the heart rate and respiratory rate from cardiovascular signals without the need for an automatic beat detection algorithm is also important. The ability to track heart rate without performing beat detection is significant since there are currently few publicly available detection algorithms for cardiovascular pressure signals such as ABP, ICP, and POX [15].

SUMMARY

In its most basic form, embodiments of the present invention provide a method, system, and apparatus to monitor cardiovascular signals such as arterial blood pressure (ABP), pulse oximetry (POX), and intracranial pressure (ICP). The system can be used to calculate and monitor useful clinical information such as heart rate, respiratory rate, pulse pressure variation (PPV), harmonic phases, pulse morphology, and for artifact removal.

In accordance to one embodiment the system uses a state-space model of cardiovascular signals and an extended Kalman filter (EKF) to simultaneously estimate and track the cardiovascular parameters of interest such as the cardiac fundamental frequency and higher harmonics, respiratory fundamental frequency and higher harmonics, cardiac component harmonic amplitudes and phases, respiratory component harmonic amplitudes and phases, and PPV.

BRIEF DESCRIPTION OF THE DRAWINGS

Disclosed embodiments are illustrated by way of example in the figures of the accompanying drawings.

DETAILED DESCRIPTION

Figure 1:
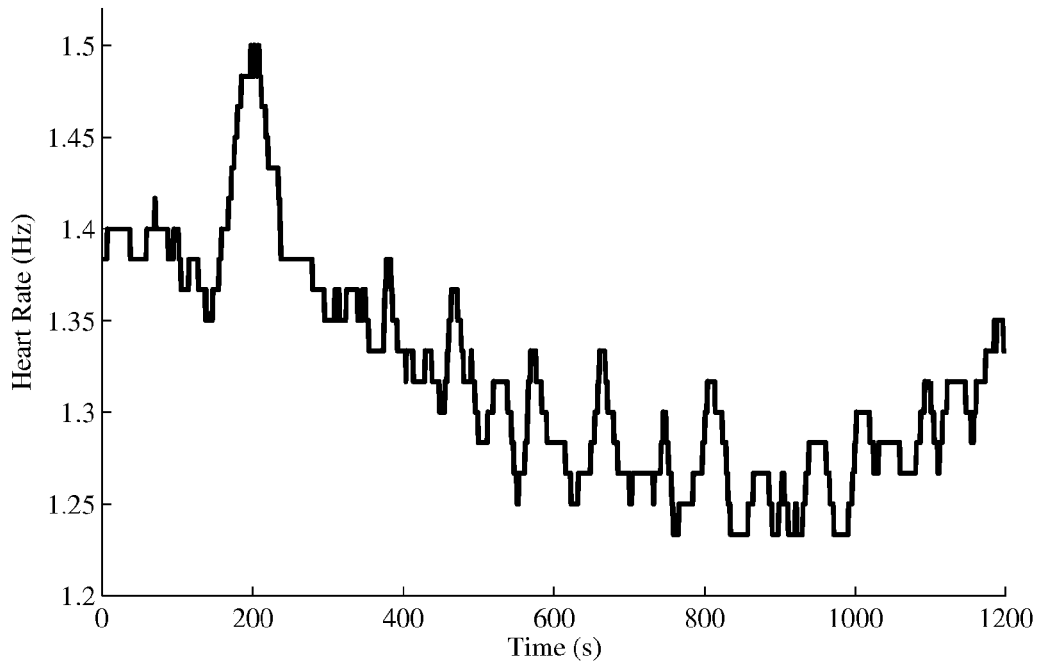
FIG. 1 illustrates estimates of the heart rate by the patient monitor from the electrocardiogram and by the EKF from the pressure signal. . . . 17
Figure 1:
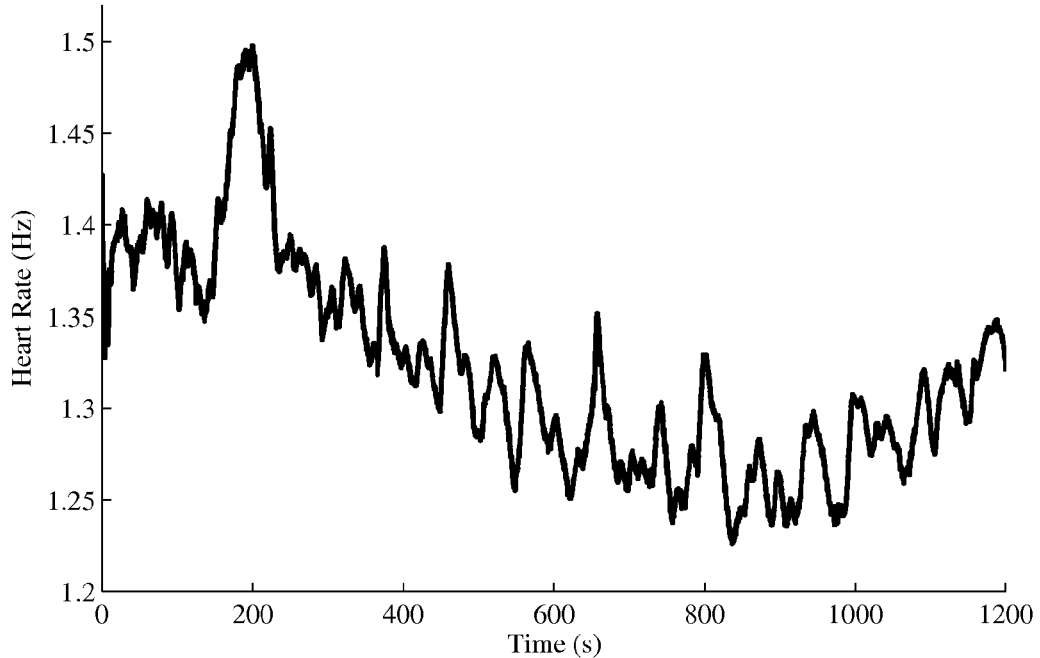

In its most basic form, embodiments of this invention provide a method, system, and apparatus based on a statistical state-space model of cardiovascular signals and the associated extended Kalman filter (EKF) algorithm to estimate parameters of clinical interest such as the cardiac fundamental frequency and higher harmonics, respiratory fundamental frequency and higher harmonics, cardiac component harmonic amplitudes and phases, respiratory component harmonic amplitudes and phases, and PPV.

Contrary to currently available systems based on isolated empirical algorithms, our proposed invention uses the EKF to estimate and track all the model parameters from arterial blood pressure (ABP) signals and solve several problems on clinical interest such as:

1. Estimation and tracking of heart rate from pressure signals.
2. Estimation and tracking of respiratory rate from pressure signals.
3. Model-based filtering, artifact removal, and interpolation.
4. Cardiovascular signal decomposition, characterization, and tracking of pulse morphology.
5. PPV estimation on mechanically ventilated subjects during periods of abrupt hemodynamic monitoring According to one embodiment, the present invention uses an extended Kalman filter (EKF) to recursively estimate the state of a linear stochastic process such that the mean squared error is minimized. The EKF is a generalization that uses local linear approximations to continuously track the estimated state in nonlinear systems. In both cases, the state is estimated in a recursive manner that has modest storage and computational requirements. Alternatively embodiments include using sigma-point filters or particle filters to perform the estimation task.

In order to apply the EKF recursions, we must first express the relationship between the variables of interest and the observed signal in state space form, $$\chi(n+1) = f[\chi(n)] + u(n) \quad (1)$$

$$y(n) = h[\chi(n)] + v(n) \quad (2)$$

where $\chi(n)$ is a vector that represents the state of the system, $u(n)$ is the process noise with a covariance matrix Q, $y(n)$ is a vector of the observed signals, and $v(n)$ is the observation or measurement noise with a variance of r. The first equation (1) is called the process or state model and (2) is called the measurement or observation model, and collectively these equations comprise the statistical state space model of the process. The most critical decision in adopting the EKF framework is to design these two models in a manner that incorporates known physiologic mechanisms and uses a compact state vector $\chi(n)$ that contains the variables of interest.

In the EKF embodiment the observation model of the cardiovascular signal consists of four primary components and is given by $$y(n) = m(n) + y_r(n) + [1 + y_p(n)] y_c(n) + v(n) \quad (3)$$

where $m(n)$ represents a low-frequency signal trend, $y_r(n)$ is a quasi-periodic respiratory signal with a fundamental frequency equal to the respiratory rate, $y_p(n)$ is another quasi-periodic signal due to respiration that causes an amplitude modulation of the cardiac component, $y_c(n)$ is a quasi-periodic cardiac signal with a fundamental frequency equal to the heart rate, and $v(n)$ is a white noise signal that accounts for the variation that is not explained by the other three components.

These four basic components are present in varying degrees in all of the cardiovascular signals that are currently monitored in clinical settings. Thus the model is versatile enough to be applied to a wide variety of signals including cardiovascular pressure signals such as central venous pressure, arterial blood pressure, and intracranial pressure; the electrocardiogram; impedance plethysmography signals; and optical reflectance or transmittance signals commonly used in pulse oximetry.

In a hospital setting patients are usually stationary and often sedated. In these cases the respiratory and heart rates are quasi-periodic signals with slowly varying fundamental frequencies, amplitudes, and morphologies. Since any periodic signal can be represented as a sum of sinusoids, one embodiment of this inventions models these signals as sums of sinusoids with slowly-varying amplitudes, phases, and frequencies, $$y_c(n) = \sum_{k=1}^{N_c} a_c^2(k, n) \sin[k\theta_c(n) + \phi_c(k, n)] \quad (4)$$

$$y_r(n) = \sum_{k=1}^{N_r} a_r^2(k, n) \sin[k\theta_r(n) + \phi_r(k, n)] \quad (5)$$

where $N_c$ and $N_r$ are the number of harmonics for the cardiac and respiratory signals, respectively; $a_c^2(k,n)$ and $a_r^2(k,n)$ are the slowly-varying amplitudes for the kth harmonic of the cardiac and respiratory signals; $\theta_c(n)$ and $\theta_r(n)$ are the instantaneous cardiac and respiratory phases; and $\phi_c(k,n)$ and $\phi_r(k,n)$ are the slowly-varying phases of the cardiac and respiratory signals. Similar models have been used in pitch tracking for speech signals.

In this model the user specifies the number of harmonics for the respiratory and cardiac signals. Generally, a large number of harmonics are necessary to accurately model the signal when sharp features are present in the signal, such as the QRS complex in an ECG signal. When the signal is smooth and nearly sinusoidal, such as the respiratory component of cardiovascular pressure signals, only a few harmonics are necessary. In general, the number of harmonics can be selected based on a spectral analysis of a representative sample of the signals of interest.

Respiratory fluctuations are known to affect most cardiovascular signals in three different ways. First, there is generally an additive respiratory component, which we model as $y_r(n)$. Second, there is often an amplitude modulation (AM), which is sometimes called pulse pressure variation or pulsus paradoxus, under pathologic conditions. The amplitude modulation can be caused by the effect of respiration on venous preload during the cardiac cycle and expansion of the arterial tree. We model this effect as an amplitude modulation of the cardiac component $y_c(n)$ in (3), which is related to the additive component through a finite impulse response (FIR) filter, $$y_p(n) = \sum_{l=0}^{N_h-1} h_p(l, n) y_r(n - l) \quad (6)$$

where $N_h$ is the number of filter coefficients specified by the user. The purpose of the FIR filter is to account for the changes in amplitudes, phases, and delay between the additive and amplitude modulation components of respiration, while maintaining the same slowly-changing fundamental frequency. Third, the respiratory component affects the heart rate through several mechanisms including vagal nerve inhibition and the baroreflex loop. We model this frequency modulation of the heart rate, which is often called respiratory sinus arrhythmia, as a frequency modulation of the heart rate. This is described in greater detail in the following section.

In the EKF embodiment of the invention, $\chi(n)$ includes all of the unknown parameters of clinical significance, $$x(n) \stackrel{\Delta}{=} \begin{bmatrix} m(n) \\ \omega_{ca}(n) \\ \theta_c(n) \\ \{a_c(k_c, n)\} \\ \{\phi_c(k_c, n)\} \\ \omega_r(n) \\ \theta_r(n) \\ \{\theta_r(n-l)\} \\ \{a_r(k_r, n)\} \\ \{a_r(k_r, n-l)\} \\ \{\phi_r(k_r, n)\} \\ \{\phi_r(k_r, n-l)\} \\ \{h_p(l, n)\} \\ \{h_f(l, n)\} \end{bmatrix} \text{ for } \begin{matrix} k_r = 1, \dots, N_r \\ k_c = 1, \dots, N_c \\ l = 1, \dots, N_{h-1} \end{matrix} \quad (7)$$

The elements of the state vector are defined in Table 1. In one embodiment of the invention the model is given by (1) where $$f[x(n)] = \begin{bmatrix} m(n) \\ \overline{\omega}_c + \alpha_c\{s_c[\omega_{ca}(n)] - \overline{\omega}_c\} \\ \theta_c(n) + T_s s_c[\omega_{cr}(n) + \omega_{ca}(n)] \\ \{a_c(k_c, n)\} \\ \{\phi_c(k_c, n)\} \\ \overline{\omega}_r + \alpha_r\{s_r[\omega_r(n)] - \overline{\omega}_r\} \\ \theta_r(n) + T_s s_r[\omega_r(n)] \\ \{\theta_r(n+1-l)\} \\ a_r(k_r, n) \\ \{a_r(k_r, n+1-l)\} \\ \phi_r(k_r, n) \\ \{\phi_r(k_r, n-l)\} \\ \{h_p(l, n)\} \\ \{h_f(l, n)\} \end{bmatrix} \quad (8)$$

$$u(n) = \begin{bmatrix} u_m(n) \\ u_{\omega_{ca}}(n) \\ 0 \\ \{u_{a_c}(k_c, n+1)\} \\ \{u_{\phi_c}(k_c, n+1)\} \\ u_{\omega_r}(n) \\ 0 \\ \{0\} \\ u_{a_r}(n) \\ \{0\} \\ u_{\phi_r}(n) \\ \{0\} \\ \{u_{h_p}(l, n+1)\} \\ \{u_{h_f}(l, n+1)\} \end{bmatrix} \quad (9)$$

TABLE 1

List of all model parameters and their initial values.

| Name | Symbol | Number | Initial |
|---|---|---|---|
| Signal Trend | m(n) | 1 | y(0) |
| Cardiac frequency (non-respiratory) | $\omega_{ca}(n)$ | 1 | $\overline{\omega}_c$ |
| Cardiac Phase | $\theta_c(n)$ | 1 | 0 |
| Cardiac Harmonic Amplitudes | $\alpha_{c,k}(n)$ | $N_c$ | Varies |
| Cardiac Harmonic Phases | $\phi_{c,k}(n)$ | $N_c$ | 0 |
| Respiratory Frequency | $\omega_r(n)$ | 1 | $\overline{\omega}_r$ |
| Respiratory Phase | $\theta_r(n-1)$ | 1 | 0 |
| Respiratory Harmonic Amplitudes | $\alpha_{r,k}(n-1)$ | $N_r$ | Varies |
| Respiratory Harmonic Phases | $\phi_{r,k}(n-1)$ | $N_r$ | 0 |
| Amplitude modulation filter coefficients | $h_p(l, n)$ | $N_h$ | 0 |
| Frequency modulation filter coefficients | $h_p(l, n)$ | $N_h$ | 0 |

The state model includes past values of the respiratory frequency, amplitudes, and phases for use in the FIR filters that are used to model the amplitude modulation and frequency modulation components of the respiratory variation.

Most of the remaining state variables are modeled as a random walk where the variance, or average step size, is controlled by the variance of the corresponding process noise term in the vector u(n), which are collectively represented in the covariance matrix Q. This is a common statistical model in adaptive filter applications when the parameters of interest are known to drift slowly over time, but an explicit statistical model based on domain knowledge is unavailable [16].

The random walk noise variances determine the tradeoff between the bias and variance of the estimates. If the noise variance for a parameter is small, the estimated value will be less sensitive to the observed signal y(n), will change more slowly over time, and may not be able to track rapid fluctuations. If the noise variance for a parameter is large, the estimated value will be more sensitive to y(n), may contain excessive variation, and will be able to track rapid fluctuations. The tradeoff between these two extremes must be made by a careful selection of the noise variance by the user.

The cardiac and respiratory instantaneous phases do not use a random walk model. If we assume that the phase components of the cardiac and respiratory harmonics, $\phi_c(k,n)$ and $\phi_r(k,n)$, are slowly varying, then in the EKF embodiment the instantaneous respiratory and cardiac frequencies are given by $$\omega(n) \stackrel{\Delta}{=} \frac{d\theta(n)}{dn} \approx \frac{\theta(n+1) - \theta(n)}{T_s} \quad (10)$$

where $T_s = f_s^{-1}$ is the sampling interval. This leads us to use the first-order difference equation as our state model for the instantaneous phases $$\theta(n+1) = \theta(n) + T_s s[w(n)] \quad (11)$$

where w(n) is the instantaneous frequency in units of radians per sample and s[w] is a saturation function that limits the range of the instantaneous frequency to known physiologic limits. One embodiment of the invention uses the clipping function $$s[\omega] = \begin{cases} \omega_{min} & \omega < \omega_{min} \\ \omega & \omega_{min} \leq \omega \leq \omega_{max} \\ \omega_{max} & \omega_{max} \leq \omega \end{cases} \quad (12)$$

The generalization to softer saturation functions is straightforward. The use of this function improves the stability of the tracking algorithm and its robustness to common types of artifact.

In the EKF embodiment the cardiac frequency is composed of two components, $$w_c(n) = w_{cr}(n) + w_{ca}(n) \quad (13)$$

where $w_{cr}(n)$ models the frequency modulation (FM) of the heart rate due to respiration, which is often called the respiratory sinus arrhythmia (RSA) or high frequency component of the heart rate variability (HRV). The second term, $w_{ca}(n)$, models the remaining heart rate variability. In the same manner as the EKF embodiment models the amplitude modulation, the FM of the heart rate is related to the additive respiratory component through an finite impulse response (FIR) filter, $$\omega_{cr}(n) = \sum_{l=0}^{N_h-1} h_f(l, n) y_r(n-l) \quad (14)$$

where $N_h$ is the number of filter coefficients specified by the user. As with the AM component, the FIR filter accounts for the changes in amplitudes, phases, and delay between the additive and FM components of respiration, while maintaining the same slowly-changing fundamental frequency.

The fluctuations in the respiratory rate $w_r(n)$ and fluctuations in the heart rate $w_{ca}(n)$ that are not due to RSA, in the EKF embodiment both modeled as a first-order autoregressive process with a mean and mild nonlinearity that limit the frequencies to know physiologic ranges, $$w_r(n+1) = \overline{w}_r + \alpha_r \{s_r[w_r(n)] - \overline{w}_r\} + u_{w_r}(n) \quad (15)$$

$$w_{ca}(n+1) = \overline{w}_c + \alpha_c \{s_c[w_{ca}(n)] - \overline{w}_c\} + u_{w_{ca}}(n) \quad (16)$$

where $\overline{w}_r$ and $\overline{w}_c$ are the a priori estimates of the expected respiratory and cardiac frequencies, respectively; $\alpha_r$ and $\alpha_c$ control the bandwidth of the frequency fluctuations; and $u_{w_r}(n)$ and $u_{w_{ca}}(n)$ are white noise processes that model the random variation in the respiratory and cardiac frequencies, respectively.

According to one embodiment, the instantaneous respiratory and heart rates in units of Hz are given by $$f_r(n) = \frac{1}{2\pi T_s} s_r[\omega_r(n)] \quad (17)$$

$$f_c(n) = \frac{1}{2\pi T_s} s_c[\omega_c(n)] \quad (18)$$

The extended Kalman filter is based on a local linear approximation of the state-space model about an estimate of the state. Other generalizations of the Kalman filter recursions to nonlinear state space models such as the unscented Kalman filter [17] and particle filters, can also be applied to this model and are considered to be alternative embodiments of the proposed system/method. [18].

According to one embodiment, the linearization is only performed during the filter portion of the algorithm. The output is linearized about the predicted estimate $\hat{\chi}(n|n-1)$, a prediction of the state at time n given only the preceding observations $\{y(n-1), \ldots, y(0)\}$. The state prediction equation is linearized about the filtered estimate $\hat{\chi}(n|n)$, an estimate of the state given the current and preceding observations $\{y(n), \ldots, y(0)\}$. In the EKF embodiment, the extended Kalman filter recursions are as follows $$H_n = J_\chi h(\chi)|_{\chi = \hat{\chi}(n|n-1)}$$

$$r_{e,n} = H_n P_{n|n-1} H_n^T + r$$

$$K_n = P_{n|n-1} H_n^T r_{e,n}^{-1}$$

$$e(n) = y(n) - h[\hat{\chi}(n|n-1)]$$

$$\hat{\chi}(n|n) = \hat{\chi}(n|n-1) + K_n e(n)$$

$$\hat{\chi}(n+1|n) = f[\hat{\chi}(n|n)]$$

$$F_n = J_\chi f(\chi)|_{\chi = \hat{\chi}(n|n)}$$

$$P_{n|n} = (I - K_n H_n) P_{n|n-1}$$

$$P_{n+1|n} = F_n P_{n|n} F_n^T + Q$$

where $J_\chi$ denotes the Jacobian operator.

To further improve robustness of the frequency estimates, the EKF embodiment includes the innovations e(n) in the clipping functions for the instantaneous phase updates to help improve stability and robustness of the system/method/apparatus, $$\hat{\theta}(n+1|n) = \theta(n|n-1) + T_s s \left[ \hat{\omega}(n|n) + \frac{1}{T_s} K_{n,\theta} e(n) \right] \quad (19)$$

where $K_{n,\theta}$ is the element of the Kalman gain vector corresponding to $\theta(n)$. This ensures that the instantaneous frequency, defined by (10), never exceeds the physiologic limits specified by the user.

The EKF embodiment requires an initial estimate of the state vector $\hat{\chi}(0|-1)$ and the initial state covariance matrix $P_{0|-1}$. The initial values of the estimated state are listed in Table 1. The initial state covariance was a diagonal matrix with 1% of the variance values listed in Table 2.

All the variables included as part of our statistical model for cardiovascular signals have a clear physiologic interpretation. Much is known about the character and range of these variables that can be used to improve the performance of the estimator. The state space modeling framework provides the means to elegantly use this type of domain knowledge to improve the estimation accuracy and tracking. Table 2 lists all of the user-specified parameters used in the EKF embodiment. The values listed in this table are those used for the first application example described later.

PPV quantifies the degree of variation in the pulsatile amplitude of arterial blood pressure signals due to respiration. It is a form of amplitude modulation of the pressure waveform caused by intrathoracic pressure fluctuations that occur with respiration. The standard method for calculating ΔPP often requires simultaneous recording of arterial and airway pressure. Pulse pressure (PP) is calculated on a beat-to-beat basis as the difference between systolic and diastolic arterial pressure. Maximal PP ($PP_{max}$) and minimal PP ($PP_{min}$) are calculated over a single respiratory cycle, which is determined from the airway pressure signal. Pulse pressure variations ΔPP are calculated in terms of $PP_{max}$ and $PP_{min}$ and expressed as a percentage, $$\Delta PP(\%) = 100 \times \frac{PP_{max} - PP_{min}}{(PP_{max} + PP_{min})/2} \quad (20)$$

The variation in the pulse pressure can also be quantified by the coefficient of variation (CV) of the pulse pressure, $$CV \triangleq \frac{\sigma_{PP}}{\mu_{PP}} \tag{21}$$

TABLE 2

User-specified model parameters in the EKF embodiment.

| Name | Symbol | Value |
|---|---|---|
| Cardiac minimum frequency | $f_{c,min}$ | 1.000 Hz |
| Cardiac mean frequency | $\bar{f}_c$ | 1.400 Hz |
| Cardiac maximum frequency | $f_{c,max}$ | 2.000 Hz |
| Cardiac cutoff frequency | $f_{c,co}$ | 0.001 Hz |
| Cardiac harmonics | $N_c$ | 6 |
| Cardiac frequency variance | $\sigma_{\omega_c}^2$ | 0.050 Hz |
| Cardiac harmonic amplitude variance | $\sigma_{\alpha_c}^2$ | 0.000 mmHg$^2$ |
| Cardiac harmonic phase variance | $\sigma_{\phi_c}^2$ | 0.000 rad$^2$ |
| Respiratory minimum frequency | $f_{r,min}$ | 0.150 Hz |
| Respiratory mean frequency | $\bar{f}_r$ | 0.250 Hz |
| Respiratory maximum frequency | $f_{r,max}$ | 0.400 Hz |
| Respiratory cutoff frequency | $f_{r,co}$ | 0.001 Hz |
| Respiratory harmonics | $N_r$ | 2 |
| Respiratory frequency variance | $\sigma_{\omega_r}^2$ | 0.050 Hz |
| Respiratory harmonic amplitude variance | $\sigma_{\alpha_r}^2$ | 0.000 mmHg$^2$ |
| Respiratory harmonic phase variance | $\sigma_{\phi_r}^2$ | 0.000 rad$^2$ |
| Trend variance | $\sigma_m^2$ | 0.500 mmHg$^2$ |
| Filter length | | 10 |
| Filter variance AM | | 0.000 |
| Filter variance FM | | 0.000 |
| Measurement noise variance | | 30.000 mmHg$^2$ |

The EKF embodiment estimates the CV as the standard deviation of $y_p(n)$, $CV=\sigma_{y_p}(n)$. Since $y_p(n)$ is the output of a linear time-varying filter with a quasi-periodic input signal, the power of $y_p(n)$ is estimated as $$\sigma_{y_p}^2(n) = \frac{1}{2}\sum_{k=1}^{N_r} a_r^4(k,n)|H_p(e^{jk\omega_r(n)},n)|^2 \tag{22}$$

where $H_p(e^{jkw_r(n)},n)$ is the frequency response of the time-varying filter $$H_p(e^{jk\omega_r(n)},n) = \sum_{l=0}^{N_h-1} h_p(l,n)e^{-jk\omega_r(n)l} \tag{23}$$

The EKF embodiment described here can be implemented as part of a digital system (e.g. computer, microprocessor or micro-controller system) to create a multitude of systems or apparatuses (alternative embodiments) for analysis and monitoring of cardiovascular signals.

While particular embodiments of the present invention have been described, it is understood that modifications and generalizations will be apparent to those skilled in the art without departing from the spirit of the invention. For instance, the statistical state-space model disclosed herein can be used in conjunction with particle filter or sigma-point filters for parameter estimation.

Operation

In this section we demonstrate versatility and utility of the invention in four applications. Specifically, we illustrate the operation and capabilities of the EKF embodiment implemented on a digital computer when used to analyzed cardiovascular signals. The EKF embodiment described here is used to estimate and track model parameters in various cardiovascular signals:

1. Arterial blood pressure (ABP) signals. This illustrates the ability of the EKF embodiment to solve three relevant problems in ABP analysis: 1) estimation and tracking of heart rate on pressure signals, 2) estimation and tracking of the respiratory rate from pressure signals, and 3) model-based filtering, artifact removal, and interpolation.
2. Pulse oximetry (POX) signals. This illustrates the ability of the EKF embodiment to solve the problem of heart and respiratory rate estimation from POX.
3. Intracranial pressure (ICP) signals. This illustrates the ability of the EKF embodiment to solve the problem of ICP pulse morphology estimation and tracking during periods of intracranial hypertension.
4. Pressure signals with pulse pressure variation (PPV). This illustrates the ability of the EKF embodiment to solve the problem of PPV estimation and tracking on mechanically ventilated subjects.

1. Heart and Respiratory Rate Estimation and Interpolation of ABP

The following application example illustrates the results obtained with the proposed EKF embodiment on a representative ABP signal, and the ability of the proposed EKF embodiment to solve three relevant problems on ABP analysis: 1) estimation and tracking of heart rate on pressure signals, 2) estimation and tracking of the respiratory rate from pressure signals, and 3) model-based filtering, artifact removal, and interpolation.

FIG. 1 shows the heart rate as estimated by an algorithm in the patient monitor from the electrocardiogram and the estimate produced by the EKF embodiment from the pressure signal. These estimates are nearly identical, and the estimate produced by the proposed EKF embodiment precedes the estimate from the patient monitor by approximately 5 s.

This example demonstrates the ability of the EKF embodiment to accurately track the heart rate and respiratory rate in pressure signals without the need for automatic beat detection algorithm. The ability to track heart rate without performing beat detection is significant since there are currently few publicly available detection algorithms for cardiovascular pressure signals such as ABP, ICP, and POX [15]. Additionally, the EKF embodiment can be used as a preprocessing algorithm to estimate the heart and respiratory rate frequencies and to eliminate signal artifact, which improves the accuracy of automatic detection algorithms [15].

2. Estimation & Tracking of Respiratory Rate from POX

The following application example demonstrates how well the EKF embodiment can track the parameters of interest, such as the heart and respiratory rates, using only an infrared absorption signal used in pulse oximetry (POX).

Figure 2:
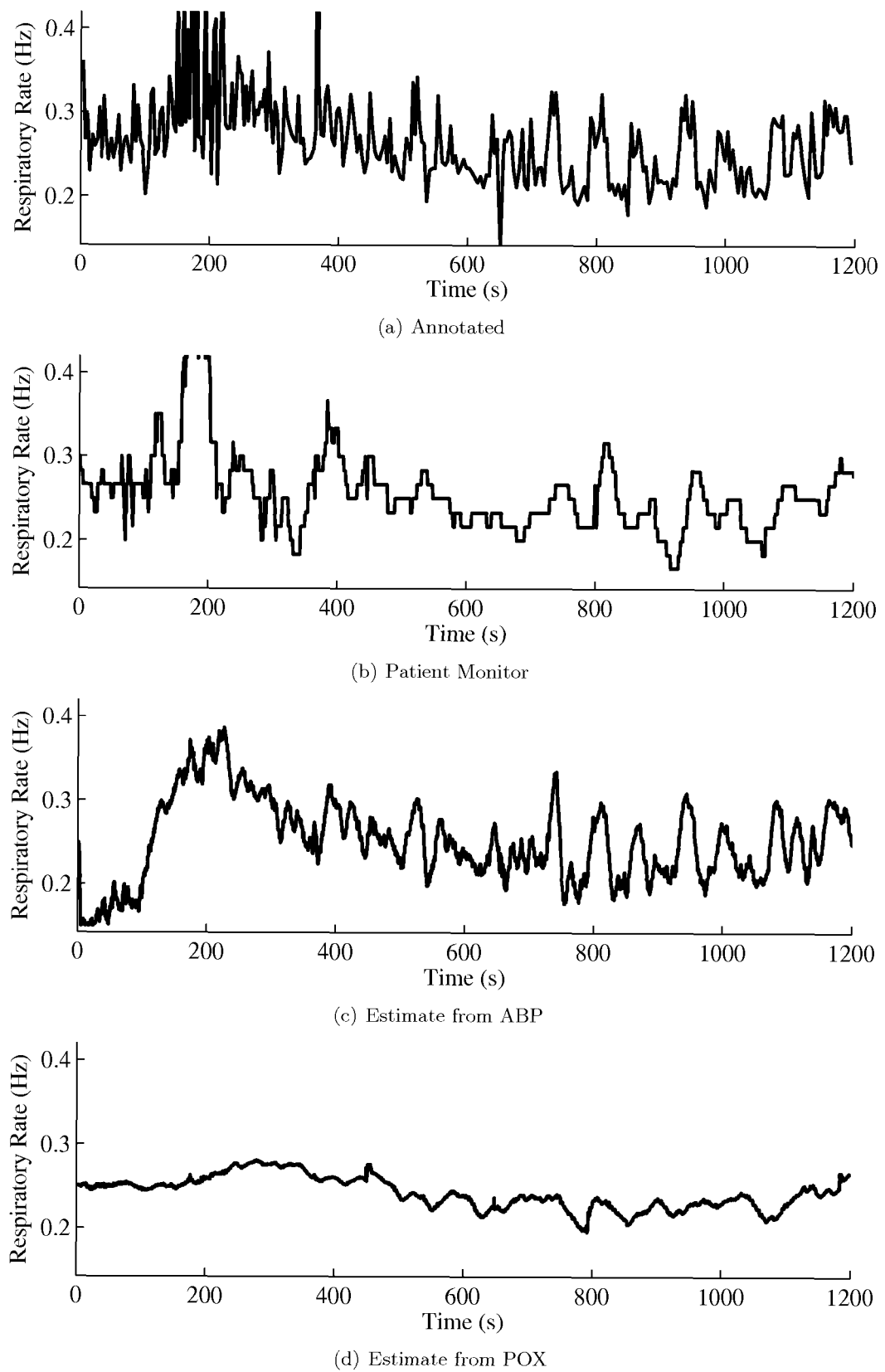
FIG. 2 illustrates estimates of the respiratory rate by manual annotations of the impedance signal acquired from the ECG leads, by the patient monitor from the ECG impedance, by the EKF from the ABP signal, and by the EKF from the POX signal. . . . 18

FIG. 2 shows four estimates of the respiratory rate. All three of the plots show an estimate of the respiratory rate based on manual annotations. The EKF embodiment is able to track the respiratory rate more accurately from the ABP signal than the patient monitor is able to track it from the impedance plethysmography signal. The estimate from the POX signal is less accurate and takes longer to begin tracking. This is partly due to the artifact in the POX signal and weaker respiratory components in this signal.

3. Tracking Changes in Pulsatile Morphology in ICP

In this example we demonstrate the ability of the EKF embodiment to track pulsatile morphology changes in ICP during a period of intracranial hypertension. Traumatic brain injury (TBI) is a leading cause of death and disability in the United States [19]. Elevated intracranial pressure often results in secondary injury due to decreased cerebral perfusion pressure and cerebral ischemia [9,20].

It is generally accepted that continuous monitoring of ICP signals has resulted in improved patient outcome [10]. Current ICP therapy is based predominantly on the mean ICP and the ICP pulse morphology. Generally, clinicians intervene to lower mean ICP when it exceeds a threshold, which is usually 20 mmHg [21]. Taken alone the mean ICP does not indicate the source of hypertension, such as poor brain compliance or impaired cerebral autoregulation (CAR) [8,22]. Determining ways to better understand and track these variables remains a significant research goal.

It is generally accepted that the ICP pulse morphology is associated with mean ICP, brain compliance, and CAR. As mean ICP increases, compliance decreases, and CAR becomes impaired, the pulse morphology is thought to undergo a "rounding" transition [7-9]. Several researchers have developed indices related to these variables that were derived from the ICP pulse morphology [8,10,11,22-24]. These indices use methods such as spectral analysis [12,13] and pulse slope [14] to quantify the ICP pulse morphology.

Figure 3:
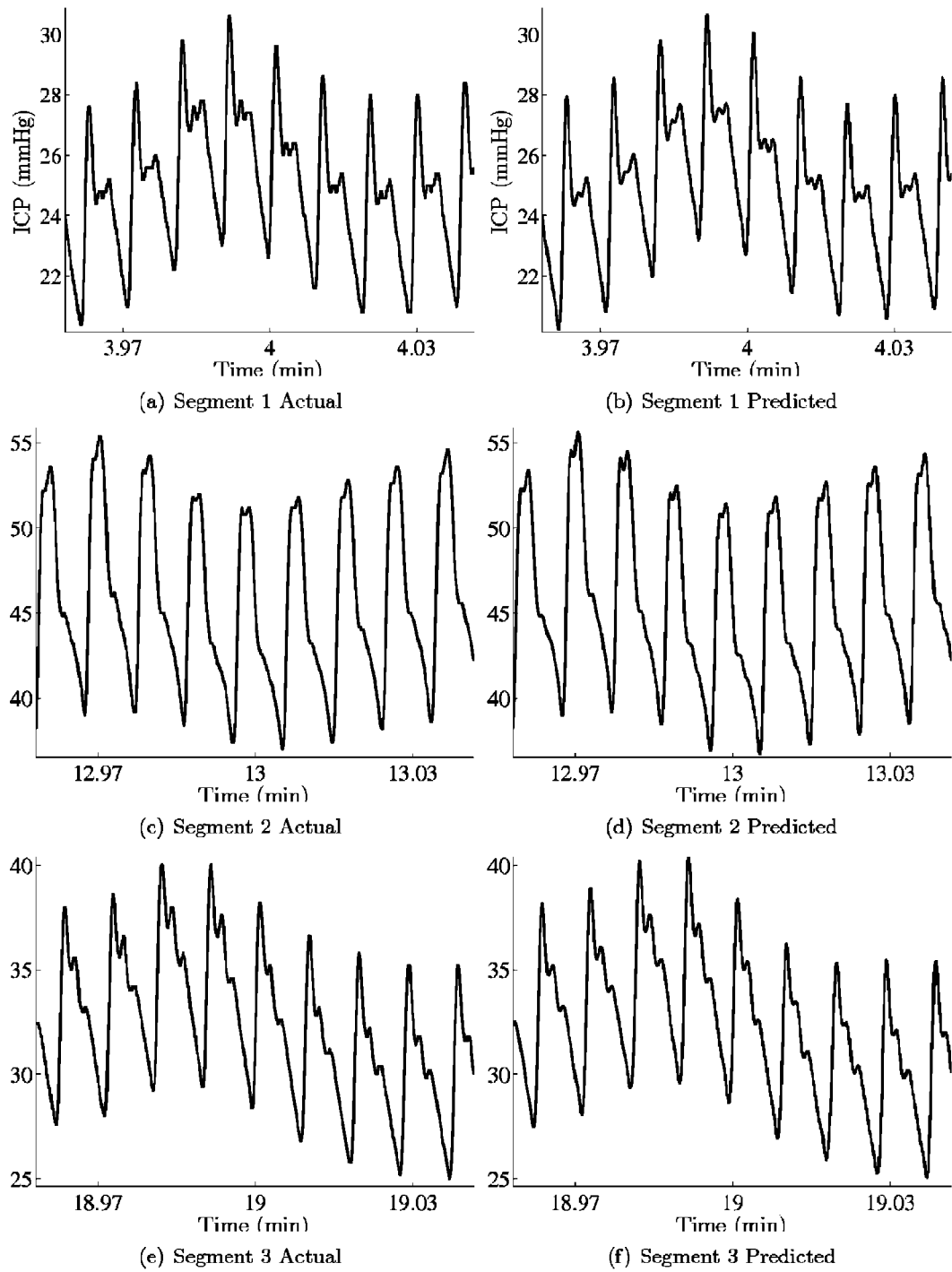
FIG. 3 shows examples of an actual and predicted intracranial pressure signal. . . . 19

The proposed EKF embodiment provides a solution to the problem of ICP pulse morphology characterization by providing the ability to estimate and track a set of parameters that can be used to characterize the ICP pulse morphology. FIG. 3 shows an example of the EKF embodiment applied to an intracranial pressure (ICP) signal acquired from an 11.5 year old male with traumatic brain injury who was admitted to Doernbecher Children's Hospital (ICP Database). The ICP signal was sampled at 125 Hz [25]. The three brief (5 s) segments shown in the top middle plot illustrate three well known changes in pulse morphology that are indicators of cerebral autoregulation and blood volume [7,22,26]. The EKF embodiment can be used to continuously track changes in amplitude and phase of the cardiac components that account for the pulse morphology. The characterization of these signal components as a compact set of metrics is a key advantage of the state space model. These components can be used to analyze and detect changes in the pulse morphology that are not easily discerned through a time domain plot or time-frequency analysis [27]. In this example we can see that as the ICP mean increases the amplitudes of the first and second cardiac harmonics increase, while all the higher harmonics stay relatively constant. More significantly, the phase relationship between the harmonics changes considerably during the period of intracranial hypertension resulting in a rounding of the pulse morphology. The proposed invention can be used to estimate and track the amplitude and phase relationship between all of the relevant harmonics in order to investigate ICP pulse morphology changes. Additionally, the EKF embodiment also track the heart rate, respiratory rate, respiratory effects on ICP, and all the other model parameters using a unified approach. The ability to estimate and track all the model parameters simultaneously using a single algorithm enables researchers to investigate the relationship of these parameters as a function of the mean ICP and pulse morphology.

4. Tracking Pulse Pressure Variation (PPV)

Numerous studies have found that pulse pressure variation (PPV) is one of the most sensitive and specific predictors of fluid responsiveness and is used to guide fluid therapy in multiple patient populations receiving mechanical ventilation [1-5]. Currently, there are few publicly available algorithms capable of estimating PPV [6].

Figure 4:
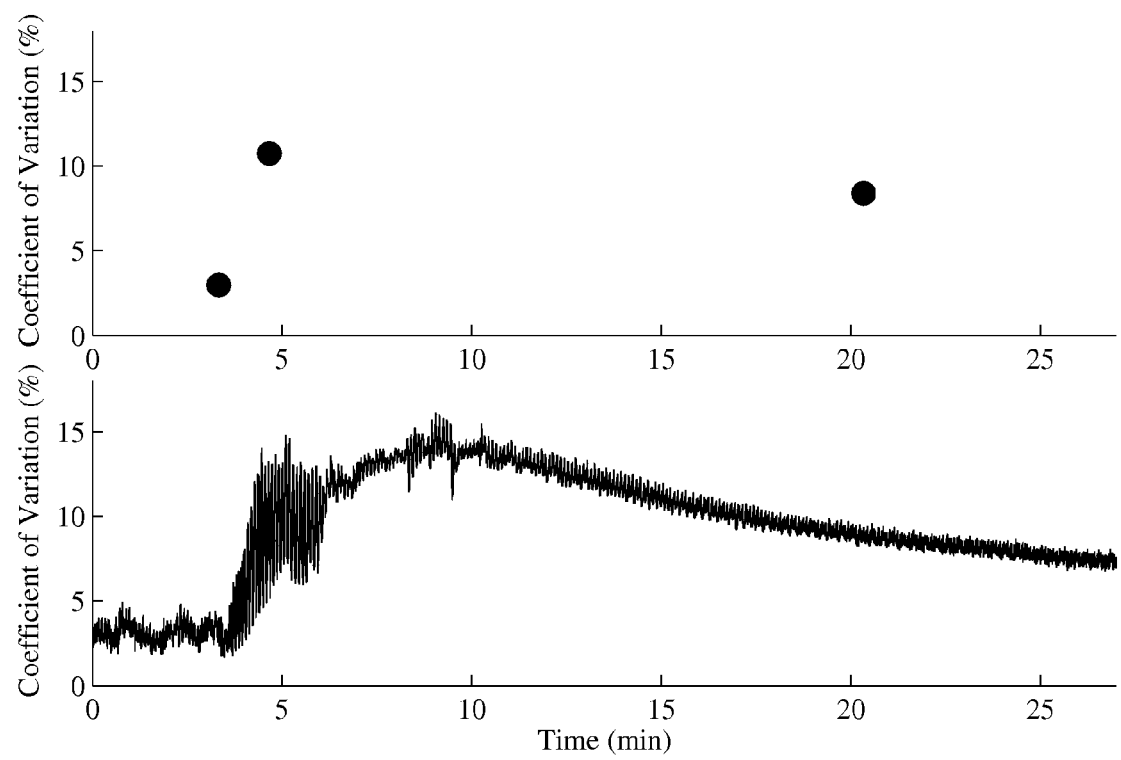
FIG. 4 shows an example of the EKF embodiment tracking pulse pressure variation (PPV) during a period of abrupt hemodynamic changes after an acute injury involving severe blood loss. The PPV estimated using the EKF embodiment (bottom plot) closely matches the expert annotations (top plot). . . . 20

FIG. 4 shows an example illustrating the ability of the EKF embodiment algorithm to estimate and track variations in PPV during a period of significant hemodynamic changes. Note how the PPV estimates obtained with the EKF embodiment are consistent with the PPV expert annotations.

What is claimed is:

1. A computer implemented method for monitoring and analysis of cardiovascular signals based on state-space estimation methods, comprising:
   (a) implementing a statistical state-space model for cardiovascular signals, said statistical model includes a method for limiting said cardiovascular signals' instantaneous frequency to physiologic limits based on enforcing limits on one or more estimated state variables, and said state-space method makes use of an instantaneous phase update clipping function based on innovations $e(n)$ to improve stability and robustness, wherein said innovations $e(n)=y(n)-h[\hat{\chi}(n|n-1)]$ are obtained by subtracting the predicted measurement $h[\hat{\chi}(n|n-1)]$ based on the predicted state $\hat{\chi}(n|n-1)$ from the observations $y(n)$;
   (b) initializing said statistical state-space model; and
   (c) processing said cardiovascular signals using a device with a processor to estimate a set of clinically relevant cardiovascular parameters based on said statistical state-space model using a state-space estimation method.

2. A method as recited in claim 1, wherein said state-space method is implemented using an Extended Kalman Filter (EKF).

3. A method as recited in claim 1, wherein said state-space method is implemented using a particle filter.

4. A method as recited in claim 1, wherein said state-space method is implemented using a sigma-point filter.

5. A method as recited in claim 1, wherein said set of clinically relevant cardiovascular parameters include heart rate, respiratory rate, pulse pressure variation, amplitude and phases of higher cardiac harmonics, amplitude and phases of higher respiratory harmonics, pulse morphology, amplitude modulation index due to respiration, and frequency modulation index due to respiration.

6. A method as recited in claim 1, wherein said statistical state-space model and said state-space estimation method is used to remove artifacts and noise from said cardiovascular signals.

7. A method as recited in claim 1, wherein said method is implemented in firmware or software as means for determining cardiovascular parameters in a cardiovascular apparatus, medical device, or cardiovascular analysis system which includes integrated means for (1) estimating and tracking heart rate from cardiovascular signals, (2) estimating and tracking respiratory rate from cardiovascular signals, (3) model-based filtering, artifact removal, and interpolation, (4) cardiovascular signal decomposition, characterization, and tracking of pulse morphology, and (5) pulse pressure variation estimation.

8. A method as recited in claim 7, wherein said method includes means for estimating and tracking pulse pressure variation in mechanically ventilated patients.

9. A method as recited in claim 1, wherein said method includes means for estimating and tracking pulse pressure variation from arterial blood pressure or plethysmography signals.

10. A method as recited in claim 9, wherein said method includes means for estimating and tracking pulse pressure variation in mechanically ventilated patients during regions of abrupt hemodynamic changes from arterial blood pressure or plethysmography signals.

11. A computer implemented method for predicting fluid responsiveness and guiding fluid therapy from cardiovascular signals, comprising:
   (a) implementing a statistical state-space model for cardiovascular signals, said statistical model includes a method for limiting said cardiovascular signals' instantaneous frequency to physiologic limits based on enforcing limits on one or more estimated state variables, and said state-space method makes use of an instantaneous phase update clipping function based on innovations e(n) to improve stability and robustness, wherein said innovations $e(n)=y(n)-h[\hat{\chi}(n|n-1)]$ are obtained by subtracting the predicted measurement $h[\hat{\chi}(n|n-1)]$ based on the predicted state $\hat{\chi}(n|n-1)$ from the observations y(n);

(b) initializing said statistical state-space model;

(b) initializing a generalized Kalman filter with initial values for said state-space model parameters;

(c) estimating pulse pressure variation parameter using said generalized Kalman filter and said statistical state-space model implemented in a device with a processor from input arterial blood pressure or plethysmography signals; and (d) predicting fluid status and guiding fluid therapy based on said pulse pressure variation parameter.

12. A medical apparatus for cardiovascular signal monitoring and analysis, comprising:

(a) a processor configured for (1) implementing a statistical state-space model for cardiovascular signals, said statistical model includes a method for limiting said cardiovascular signals' instantaneous frequency to physiologic limits based on enforcing limits on one or more estimated state variables, and said state-space method makes use of an instantaneous phase update constrain function based on innovations e(n) to improve stability and robustness, wherein said innovations $e(n)=y(n)-h[\hat{\chi}(n|n-1)]$ are obtained by subtracting the predicted measurement $h[\hat{\chi}(n|n-1)]$ based on the predicted state $\hat{\chi}(n|n-1)$ from the observations y(n); (2) initializing said statistical state-space model; and (3) processing said cardiovascular signals using a device with a processor to estimate a set of clinically relevant cardiovascular parameters based on said statistical state-space model using a state-space estimation method.

13. The apparatus of claim 12, wherein said state-space method is implemented using an Extended Kalman Filter (EKF).

14. The apparatus of claim 12, wherein said state-space method is implemented using a particle filter.

15. The apparatus of claim 12, wherein said state-space method is implemented using a sigma-point filter.

16. The apparatus of claim 12, wherein said set of clinically relevant cardiovascular parameters include heart rate, respiratory rate, pulse pressure variation, amplitude and phases of higher cardiac harmonics, amplitude and phases of higher respiratory harmonics, pulse morphology, amplitude modulation index due to respiration, and frequency modulation index due to respiration.

17. The apparatus of claim 12, wherein said statistical state-space model and said state-space estimation method is used to remove artifacts and noise from said cardiovascular signals.

18. The apparatus of claim 12, wherein said method is implemented as means for (1) estimating and tracking heart rate from cardiovascular signals, (2) estimating and tracking respiratory rate from cardiovascular signals, (3) model-based filtering, artifact removal, and interpolation, (4) cardiovascular signal decomposition, characterization, and tracking of pulse morphology, and (5) pulse pressure variation estimation.

19. The apparatus of claim 12, wherein said method includes means for estimating and tracking pulse pressure variation from arterial blood pressure or plethysmography signals.

20. The apparatus of claim 19, wherein said method includes means for estimating and tracking pulse pressure variation in mechanically ventilated patients.

* * * * *